Oct. 1, 1974 E. C. THINGHOLM Plant Pat. 3,630
BOUGAINVILLEA
Filed June 26, 1973
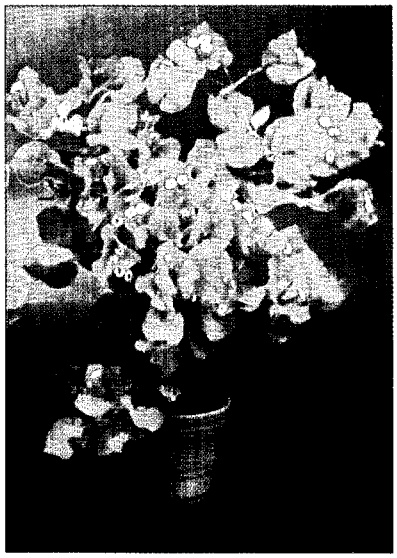

United States Patent Office

Plant Pat. 3,630
Patented Oct. 1, 1974

3,630

BOUGAINVILLEA

Ejner C. Thingholm, 5270 Naesby, Allesoe, Denmark

Filed June 26, 1973, Ser. No. 373,716
Int. Cl. A01h 5/00
U.S. Cl. Plt.—54 1 Claim

ABSTRACT OF THE DISCLOSURE

A new, asexually reproduced variety of bougainvillea plant having a distinct purple-red color of bracts which color remains substantially unchanged from the unfolding and a considerably darker color of bracts and foilage than the mother plant "Killie Campbell" from which it was reproduced.

The present invention relates to a new and distince variety of bougainvillea plant which was discovered by me as a mutant of "Killie Campbell," grown by me in my cultivated commercial nursery gardens, located in Allesoe, Denmark.

For 10 years I have grown for sale the bougainvillea plant "Killie Campbell," the flowers of which are orange after unfolding, but later turning into a purple red color. In 1968 I found a mutant deviating considerably in color of bracts and of foilage and having bracts presenting a most distinctive and highly attractive appearance. The mutation does not have the orange-red tinge on bracts and foilage known from "Killie Campbel." The mutation is stable in growth as well as in color. I intend to call it "Ametyst." Continued close observations of this outstanding plant in my greenhouse convinced me, that it represents a new and distinct variety unlike any other formerly known to me or previously reported or described in published literature, as evidenced by the following unique combination of features which are outstanding in my new mutation:

(1) A floral structure with large bracts having a distinct and uniform purple-red color, which remains unchanged from the unfolding and (2) a distinct dark foilage.

Asexual reproduction of my new bougainvillea variety by own-rooted cuttings, as grown by me in my greenhouse in Allesoe shows that the aforementioned characteristics and distinctions come true and are established and transmitted through succeeding propagations.

The acompanying drawing shows typical specimens of the floral stems, foilage and inflorescences of my new bougainvillea variety as depicted in color as nearly true as it is reasonably possible to make the same in color illustration of this character.

The following is a detailed description of my new bougainvillea variety, with color terminology in accordance with the Royal Horticultural Society's Colour Chart and Nomenclature except where general color terms of ordinary dictionary significance are obvious.

Parentage: A mutation of "Killie Campbell."
Location where grown and observed: Allesoe, Denmark.

PLANT

Growth:

*Habit.*—Upright-spreading; semi-scandent.
*New stems.*—1–2 mm. in diameter; glabrescent.
*Color.*—Greenish-brown.
*Older stems and branches.*—Heavy treelike with longitudinal fissures. Color—light green when young; at maturity greenish grey and fissured.
*Spines.*—Situated in axil over bud; strong up to 12 mm. long.

Leaves:

*Internodes.*—About 20–50 mm. in length; leaves alternate.
*Texture.*—Thin, puberulate when young; glabrate at maturity.
*Size.*—Lamina, excluding leaves at base of branches. Long—from 50–100 mm., average 62 mm.; wide, 25–55 mm., average 35 mm.
*Petiole.*—Rounded rim; flat upper side, glabrescent. Veins visible on upper side in whole length of the petioles. Long—from 15–30 mm., average 20 mm. Color—green.
*Shape.*—Subcordate; margins entire.
*Upper surface.*—Almost dull. Color—green, near RHS 147A.
*Lower surface.*—Almost dull. Color—green RHS 147B, color of veins—brown 166A.

INFLORESCENCE

Position and abundance: Inflorescences—normally 3 per flowering branch; but up to 9 is not infrequent; in the wintertime the inflorescence is less, 1 or 2 per flowering branch are not infrequent; rich flowering.

Habit: Each inflorescence branch indeterminate and branching racemose. The pedicles having a lossening layer on the middle of the side-flower pedicles.

Axes: Inflorescence axis terete; color—green, RHS 148A.
*Length to first ramification.*—45–75 mm.

Bracts:

*Arrangement.*—Mostly alternate.
*Number.*—3.
*Habit.*—Sessile.
*Size.*—35–65 mm. long, average 48 mm., and 25–50 mm. wide, average 38 mm.
*Shape.*—Subcordate.
*Texture.*—Plain; veins evident and raised above surface prominently.
*Color.*—Lively purple red RHS 74A. Veins brown 166A.

Flowers:

*Size.*—Length 15–25 mm.
*Position.*—8–12 mm. from base of the bracts lamina.
*Filaments.*—Normally 8 green filaments with yellow sacs.
*Style.*—Long, green.
*Color.*—The Corolla tube red-purple RHS 71A. On buds purple-red top 74A. The Corolla white-yellow, RHS 2D. The lobes of the Corolla tube yellow-green RHS 144B towards the center.

I claim:

1. A new and distinct variety of bougainvillea plant substantially as herein shown and described, characterized particularly as to novelty by a distinct and attractive purple-red color of bracts which color remains substantially unchanged from the unfolding and a considerably darker color of bracts and of foilage than the mother plant "Killie Campbell."

No references cited.

ROBERT E. BAGWILL, Primary Examiner

UNITED STATES PATENT OFFICE

CERTIFICATE OF CORRECTION

Patent No. Plant Pat. 3,630 Dated October 1, 1974

Inventor(s) Ejner C. Thingholm

It is certified that error appears in the above-identified patent and that said Letters Patent are hereby corrected as shown below:

Col. 1, line 17, "distince" should be -- distinct --.
Col. 1, line 29, "Campbel" should be -- Campbell --.
Col. 1, line 47, "acompanying" should be --accompanying --

Signed and sealed this 7th day of January 1975.

(SEAL)
Attest:

McCOY M. GIBSON JR.
Attesting Officer

C. MARSHALL DANN
Commissioner of Patents